US012690941B2

(12) United States Patent
McGinley et al.

(10) Patent No.: US 12,690,941 B2
(45) Date of Patent: Jul. 28, 2026

(54) INTEGRATED TIME-INDICATING DEVICE DURING TOPICAL SKIN APPLICATION

(71) Applicant: CareFusion 2200, Inc., San Diego, CA (US)

(72) Inventors: Christopher McGinley, San Diego, CA (US); Moises Ortiz, San Diego, CA (US); Camille A. Sendlak, San Diego, CA (US); Brandon Toth, San Diego, CA (US); Richard Meng, San Diego, CA (US); Dan Zimbler, San Diego, CA (US)

(73) Assignee: CAREFUSION 2200, INC., San Diego, CA (US)

( * ) Notice: Subject to any disclaimer, the term of this patent is extended or adjusted under 35 U.S.C. 154(b) by 545 days.

(21) Appl. No.: 18/021,878

(22) PCT Filed: Aug. 13, 2021

(86) PCT No.: PCT/US2021/045923
§ 371 (c)(1),
(2) Date: Feb. 17, 2023

(87) PCT Pub. No.: WO2022/046437
PCT Pub. Date: Mar. 3, 2022

(65) Prior Publication Data
US 2023/0301746 A1 Sep. 28, 2023

Related U.S. Application Data

(60) Provisional application No. 63/071,129, filed on Aug. 27, 2020.

(51) Int. Cl.
*A61B 90/80* (2016.01)
*A61B 90/00* (2016.01)
(Continued)

(52) U.S. Cl.
CPC ............... *A61B 90/80* (2016.02); *A61L 2/18* (2013.01); *A61L 2/28* (2013.01);
(Continued)

(58) Field of Classification Search
CPC ............ A61B 90/80; A61B 2090/0807; A61L 2/0088; A61L 2/28; A61M 35/006
(Continued)

(56) References Cited

U.S. PATENT DOCUMENTS

| | | | | |
|---|---|---|---|---|
| 4,388,936 A | * | 6/1983 | Roberts | ................. A45D 34/00 D28/91.1 |
| 2004/0111070 A1 | * | 6/2004 | Hanley | ................ A61F 9/0008 604/295 |

(Continued)

FOREIGN PATENT DOCUMENTS

| | | | | |
|---|---|---|---|---|
| CN | 210674001 U | | 6/2020 | |
| WO | WO-2020028289 A1 | * | 2/2020 | ............ A61M 5/427 |

OTHER PUBLICATIONS

International Search Report in PCT/US2021/045923, mailed Nov. 23, 2021, 7 pages total.

*Primary Examiner* — Andrew J Mensh
(74) *Attorney, Agent, or Firm* — Arent Fox LLP and Care Fusion

(57) ABSTRACT

An applicator having a body configured to house a fluid, an application member in selective fluid communication with the body, and a time-indicating device, wherein the time-indicating device includes a capillary component having a fluid path, wherein the time-indicating device is configured such that fluid advancement along the fluid path directly or indirectly provides at least a first observable signal, and wherein the first observable signal signifies a first certain application period.

16 Claims, 6 Drawing Sheets

(51) Int. Cl.

| | |
|---|---|
| *A61L 2/18* | (2006.01) |
| *A61L 2/28* | (2006.01) |
| *A61L 103/05* | (2026.01) |
| *A61M 35/00* | (2006.01) |

(52) U.S. Cl.

CPC ... *A61B 2090/0807* (2016.02); *A61L 2103/05* (2026.01); *A61L 2202/15* (2013.01); *A61M 35/006* (2013.01)

(58) Field of Classification Search

USPC ........................................................ 604/290

See application file for complete search history.

(56) References Cited

U.S. PATENT DOCUMENTS

| | | | |
|---|---|---|---|
| 2004/0179888 A1 | 9/2004 | Tufts et al. | |
| 2010/0168638 A1* | 7/2010 | Korogi ................ | A61M 35/006 401/133 |
| 2013/0202482 A1 | 8/2013 | Froimson | |
| 2015/0098861 A1 | 4/2015 | Degala et al. | |
| 2018/0161560 A1* | 6/2018 | Souza ................... | A61B 90/80 |

* cited by examiner

INTEGRATED TIME-INDICATING DEVICE DURING TOPICAL SKIN APPLICATION

CROSS-REFERENCE TO RELATED APPLICATIONS

This application is a National Phase of PCT Application No. PCT/US2021/045923, filed Aug. 13, 2021, which claims the benefit of U.S. Provisional Application No. 63/071,129, filed Aug. 27, 2020, the disclosures of each of which are hereby incorporated by reference in their entireties.

TECHNICAL FIELD

The present disclosure is directed to time-indicating devices configured for use with a fluid applicator, particularly a fluid applicator for applying an antiseptic solution.

BACKGROUND

In the art of antiseptic solutions, application time can have a significant impact on the log reduction in microbial load. Efficacy studies conducted with a specific antiseptic product follow a specific application time, and the replication of this application time by the health care practitioner is critical to achieving the desired microbial kill.

It can be challenging to adhere to a labeled application time. In practice, application time is frequently significantly shorter than the product label application when health care practitioners do not use a timing device. However, the use of external timing devices (e.g., a clock) incurs additional procedure steps, which increases the risk of health care practitioners inadvertently missing steps, particularly when performing procedures that inherently require a number of steps, such as the preparation of a patient's skin prior to surgery and/or a needle stick. Furthermore, the use of external timing devices may also lead to application failure modes in which a health care practitioner inadvertently omits to check the start or ending time of application. In addition, the use of external timing devices may require a health care practitioner to divert attention away from the procedural surface, such as a surgical patient's skin.

There is thus a need in the art for a time-indicating device the ensures adherence to labeled application times without the drawbacks of external timing devices.

SUMMARY

The present disclosure is directed to a time-indicating device configured for use with a fluid applicator, particularly a fluid applicator for applying an antiseptic solution. According to some aspects, the time-indicating device comprises a capillary component having at least one fluid path along which a fluid may advance via capillary action. The time-indicating device of the present disclosure may be configured to provide at least a first observable signal upon a certain physical and/or chemical event, wherein the first observable signal signifies the end of a first certain application period.

DETAILED DESCRIPTION

Figure 1:
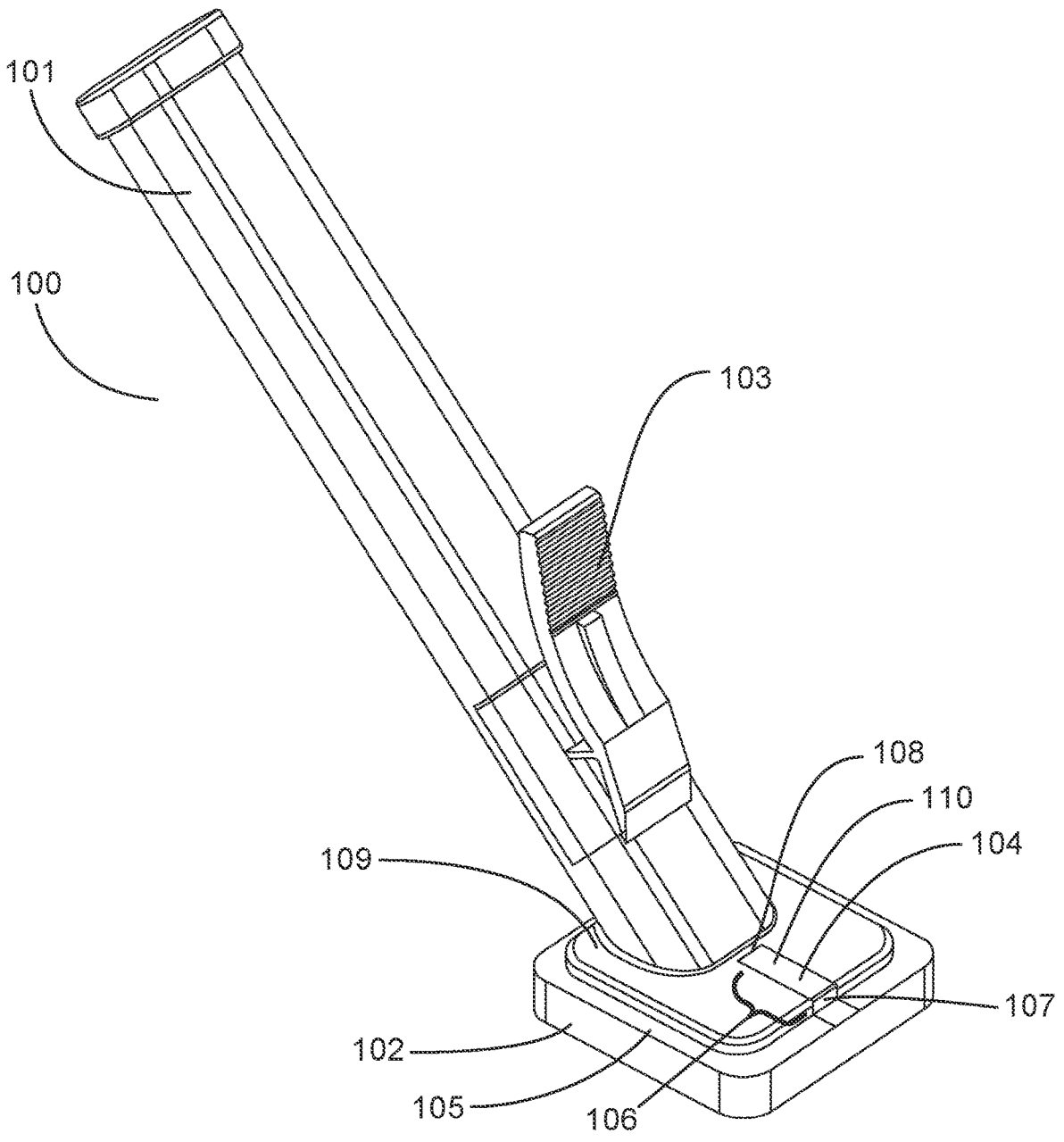
FIG. 1 shows an example applicator comprising a time-indicating device, according to aspects of the present disclosure.

The present disclosure is directed to a time-indicating device configured for use with a fluid applicator, particularly a fluid applicator for applying an antiseptic solution. According to some aspects, the time-indicating device comprises a capillary component having at least one fluid path along which a fluid may advance via capillary action. The time-indicating device of the present disclosure may be configured to provide at least a first observable signal upon a certain physical and/or chemical event, wherein the first observable signal signifies the end of a first certain application period. According to some aspects, the time-indicating device of the present disclosure may be configured to provide a second, third, or more observable signal in order to signify the end of a second, third, or more application period, respectively.

As used herein, the terms "fluid applicator" and "applicator" refer to a device having at least a body and an application member, wherein the body is configured to house a fluid (such as an antiseptic solution) and is in selective fluid communication with the application member such that fluid may be selectively delivered from the body to the application member. According to some aspects, the application member is a component configured to apply the fluid to a surface, such as a foam sponge material or any suitable material that allows the application of fluid to a surface external to the applicator.

According to some aspects, the body of the applicator may house one or more ampoules and/or similar containers in which the fluid, such as an antiseptic solution, may be contained prior to application to a surface. The applicator may further comprise a fluid metering device, such as a pledget, configured to at least partially control and/or direct the flow of the fluid from the body to the application member when the applicator is in use. The applicator may optionally comprise an actuator configured to actuate the applicator, wherein actuation of the applicator corresponds to the body being provided in fluid communication with the application member as described herein.

Non-limiting example applicators that may be used according to the present disclosure may be found, for example, in Applicant's co-pending U.S. application Ser. No. 15/163,500 and in U.S. Pat. Nos. 5,690,958; 6,536,975; 8,708,983; 8,899,859; 9,119,946; 9,572,967; 9,757,551; 9,968,764; 10,076,648; and 10,549,078, the disclosures of which are incorporated herein by reference in their entirety.

According to some aspects, the fluid as described herein may comprise an antiseptic solution, wherein the antiseptic solution comprises at least one antiseptic agent and a solvent. According to some aspects, the antiseptic solution is an aqueous solution. As used herein, the term "aqueous solution" refers to a solution wherein the solvent comprises at least a majority of water. According to some aspects, the antiseptic solution is an alcoholic solution. As used herein, the term "alcoholic solution" refers to a solution wherein the solvent comprises at least a majority of alcohol.

As used herein, the term "antiseptic agent" refers to a chemical component that deactivates, inhibits, or otherwise destroys the unacceptable action of a microorganism. According to some aspects, the antiseptic agent may comprise a cationic molecule (i.e., a molecule having a positive charge), such as a cationic surfactant or a cationic biguanide derivative (i.e., a compound derived from biguanide). According to some aspects, the antiseptic agent may comprise a bis-(dihydropyridinyl)-decane derivative (i.e., a compound derived from bis-(dihydropyridinyl)-decane). According to some aspects, the antiseptic agent may comprise an octenidine salt and/or a chlorhexidine salt. Non-limiting examples of antiseptic agents useful according to the present discourse include octenidine dihydrochloride, chlorhexidine gluconate, alexidine, and any combination thereof.

Additionally or alternatively, the antiseptic agent may comprise iodine. According to some aspects, the iodine may be provided as an iodine complex, such as povidone-iodine (PVPI), nonylphenoxy-(ethyleneoxy)-iodine, polyethylene oxy polyprop leneoxy-iodine, undecoylinium-chloride-iodine, iodine povacrylex, and combinations thereof.

According to some aspects, the concentration of a single antiseptic agent or the cumulative concentration of two or more antiseptic agents in the antiseptic solution may be from about 0.0001% to about 2.0% w/v, optionally from about 0.01% to about 1.0% w/v, optionally from about 0.1% to about 0.4% w/v. According to some aspects, the concentration of a single antiseptic agent or the cumulative concentration of two or more antiseptic agents in the antiseptic solution may be from about 0.0001% to about 0.4% w/v, and optionally from about 0.1% to about 0.2% w/v. According to some aspects, the concentration of a single antiseptic agent or the cumulative concentration of two or more antiseptic agents in the antiseptic solution may be from about 0.1% to about 2.0% w/v, optionally from about 0.5% to about 2.0% w/v, and optionally about 2.0% w/v. According to some aspects, the concentration of a single antiseptic agent or the cumulative concentration of two or more antiseptic agents in the antiseptic solution may be from about 0.1% to about 15.0% w/v, optionally from about 0.1% to about 10.0% w/v, optionally from about 5.0% to about 10.0% w/v, optionally from about 10.0% to about 15.0% w/v, optionally about 13% w/v, and optionally about 8.5% w/v.

It should be understood that the concentrations disclosed herein may correspond with the concentration of one or more antiseptic agents having one or more active components. For example, an antiseptic agent comprising povidone-iodine has an active component comprising iodine. In this example, the concentration of the antiseptic agent active component may be less than the concentration of the antiseptic agent.

According to some aspects, the concentration of a single antiseptic agent active component or the cumulative concentration of two or more antiseptic agent active components in the antiseptic solution may be from about 0.01% to about 5.0% w/v, optionally from about 0.01% to about 2.5% w/v, optionally from about 0.01% to about 2.0% w/v, optionally from about 0.5% to about 1.5% w/v, and optionally about 1.0% w/v.

According to some aspects, the solvent may comprise an alcohol. Non-limiting examples of alcohols include ethanol, propanol, isopropyl alcohol, and combinations thereof. According to some aspects, the concentration of alcohol in the antiseptic solution may be from about 50% to about 90% v/v, optionally from about 70% to about 80% v/v, and optionally about 70% v/v. According to some aspects, the concentration of alcohol in the antiseptic solution may be from about 10% to about 50% v/v, and optionally from about 20% to about 30% v/v. According to some aspects, the solvent may consist of alcohol.

Additionally or alternatively, the solvent may comprise water. According to some aspects, the concentration of water in the antiseptic solution may be from about 10% to about 50% v/v, and optionally from about 20% to about 30% v/v. According to some aspects, the concentration of water in the antiseptic solution may be from about 50% to about 90% v/v, and optionally from about 70 to about 80% v/v. According to some aspects, the solvent may consist of water.

According to some aspects, the antiseptic solution may further comprise a film-forming polymer. Non-limiting examples of film-forming polymers include ethyl cellulose, hydroxypropyl methylcellulose, iodine povacrylex, and acrylate polymers, such as acrylamide polymers, octylacrylamide polymers, methacrylate polymers, carboxyacrylate polymers, and polymers having dimethylaminoethyl methacrylate, butyl methacrylate, and methyl methacrylate side groups. The concentration of film-forming polymer may be varied depending on the particular solvent and antiseptic agent present in the antiseptic solution.

According to some aspects, the concentration of film-forming polymer in the antiseptic solution may be from about 0.1% to about 5% w/v, optionally from about 0.2% to about 3.0% w/v, optionally from about 0.5% to about 2.0% w/v, and optionally from about 0.75% to about 2.5% w/v.

Example acrylate polymers include, but are not limited to, DERMACRYL® AQF (2-propenoic acid, 2-methyl-, polymer with butyl 2-propenoate and methyl 2-methyl-2-propenoate), DERMACRYL® 79P (2-propenoic acid, 2-methyl-, 2-methylpropyl ester, polymer with 2-propenoic acid and N-(1,1,3,3tetramethylbutyl)-2-propenamide), each manufactured by Akzo Nobel Coatings Inc, and EUDRAGIT® E PO (poly(butyl methacylate-co-(2-dimethylaminoethyl) methacrylate-co-methyl methacrylate) manufactured by Evonik Industries. DERMACRYL® 79P is a hydrophobic, high molecular weight carboxylated acrylic copolymer. EUDRAGIT® E PO is a cationic copolymer based on dimethylaminoethyl methacrylate, butyl methacrylate, and methyl methacrylate According to some aspects, the antiseptic solution may further comprise a tinting agent. In some non-limiting examples, the tinting agent may comprise an anionic tinting agent, such as an anionic dye. The anionic dye may be any dye suitable for medical use, such as dyes approved by the Food and Drug Administration for use in food, drugs, and/or cosmetics (i.e., "D&C" or "FD&C" dyes). Example anionic dyes include, but are not limited to, FD&C Blue No. 1 (Brilliant Blue FCF), FD&C Blue No. 2 (Indigo Carmine), FD&C Green No. 3 (Fast Green FCF), FD&C Red No. 3 (Erythrosine), FD&C Red No. 40 (Allura Red), FD&C Yellow No. 5 (Tartrazine), FD&C Yellow No. 6 (Sunset Yellow FCF), D&C Yellow No. 8 (Fluorescein), D&C Orange No. 4, and combinations thereof. Combinations may be implemented to arrive at a particular color. For example, an orange tint may comprise both FD&C Red No. 40 and D&C Yellow No. 8.

According to some aspects, the concentration of tinting agent in the antiseptic solution may be from about 0.01% to about 0.15% w/v, optionally from about 0.03% to about 0.12% w/v, and optionally from about 0.05% to about 0.09% w/v.

According to some aspects, the antiseptic solution may include one or more plasticizers. The plasticizer may be an ester of an organic acid, for example, triethyl citrate and dibutyl sebacate. The concentration of plasticizer in the antiseptic solution may be from about 0.05% to about 2.0% w/v, optionally from about 0.75% to about 1.5%, and optionally from about 0.1% to about 1.0% w/v.

According to some aspects, the antiseptic solution may be the solution used in ChloraPrep™ applicators, which comprises about 2% w/v chlorhexidine gluconate in a solvent comprising about 70% v/v isopropyl alcohol and water.

It should be understood that according to some aspects, one or more components comprised by the antiseptic solution may provide two or more functions as described herein. For example, the antiseptic solution may comprise an alcohol as described herein, which may function as both a solvent and as an antiseptic agent as described herein. In another example, the antiseptic solution comprise iodine povacrylex as described herein, which may function as both an antiseptic agent and a film-forming polymer as described herein.

As described herein, the time-indicating device comprises a capillary component having at least one fluid path along which a fluid may advance via capillary action. As used herein, the term "capillary action" refers to the action of a fluid flowing into and through a space without the assistance of and/or in opposition to external forces such as gravity.

The capillary component may be configured to provide at least one observable signal in response to a certain physical and/or chemical event. Examples of observable signals include, but are not limited to, a change in the capillary component's size, a change in the capillary component's position, a change in the capillary component's color, a change in the capillary component's color intensity, and combinations thereof.

According to some aspects, the time-indicating device may further comprise one or more signaling components that function in conjunction with the capillary component. If the time-indicating device comprises one or more signaling components, the observable signal may additionally or alternatively comprise a change in the signaling component's color, a change in the signaling component's color intensity, a change in the signaling component's position relative to the capillary component, the visibility of the signaling component to a user, and combinations thereof.

In one non-limiting example, the capillary component may comprise a sorbent. As used herein, the term "sorbent" refers to a material configured to absorb and/or adsorb a fluid. Examples of sorbents useful according to the present disclosure include, but are not limited to, silica gel, aluminum oxide, cellulose, paper, titanium oxide, polyurethane foam, natural textiles, synthetic textiles, and combinations thereof. According to some aspects, the capillary component may comprise a base material on which the sorbent is provided. For example, the capillary component may comprise a sheet of base material with a coating of sorbent as described herein. According to some aspects, the base material may be a non-sorbent, that is, a material that does not absorb and/or adsorb a fluid as described herein. Examples of base materials useful according to the present disclosure include, but are not limited to, glass, plastic, metals (such as an aluminum foil), alloys, and combinations thereof.

According to some aspects, the sorbent may be provided in fluid communication with the application member of an applicator such that, upon actuation of the applicator, a portion of the antiseptic solution is absorbed and/or adsorbed by the sorbent. FIG. 1 shows an example applicator 100 having a body 101, an application member 102, and an actuator 103 as described herein. In this example, applicator 100 comprises a capillary component 104 provided proximal surface 105 of application member 102, surface 105 of application member 102 being proximal a point of fluid delivery from body 101 to application member 102 (e.g., a surface proximal an entry to a fluid conduit, not shown).

In the example shown in FIG. 1, when fluid (such as an antiseptic solution) is delivered from body 101 to application member 102 upon actuation of the applicator, a portion of the delivered fluid is absorbed and/or adsorbed by capillary component 104 along a fluid path of the sorbent via capillary action.

According to some aspects, fluid advancement along the fluid path of the capillary component may indirectly or directly provide at least a first observable signal, as described herein. For example, fluid advancement along the fluid path may correspond with a change in color and/or color intensity of the capillary component, for example, via physical wetting of the sorbent upon contact with the fluid and/or via a chemical reaction between the sorbent and a component of the fluid (e.g., a solvent or antiseptic agent as described herein). In this example, the observable signal may comprise a color and/or color intensity change of the capillary component that signifies a certain degree of fluid advancement along the fluid path of the capillary component.

In one non-limiting example, capillary component 104 of FIG. 1 may comprise a sheet of base material with a coating of sorbent thereon as described herein. As shown in FIG. 1, capillary component 104 may be provided on and/or as a portion of a flange component 109 of body 101, flange component 109 being configured to interface with application member 102. In this example, the sorbent coating may be in fluid communication with application member 102 at least at a first end 107 thereof such that, upon actuation of the applicator, a portion of the fluid delivered to application member 102 is absorbed and/or adsorbed by the sorbent. Fluid advancement along the length 106 of capillary component 104 may be observable as a color change of the sorbent. In this example, the observable signal may be a complete color change of the sorbent, thus indicating about 100% fluid advancement along the fluid path, that is, indicating that fluid has advanced about the entire length 106 of capillary component 104.

It should be understood, however, that the arrangement and operation of the time-indicating device described above is not particularly limiting. For example, capillary component 104 as shown in FIG. 1 may comprise a sorbent without a base material. In this example, the fluid path may extend from the surface of capillary component 104 that interfaces application member 102 (i.e., the surface opposite top surface 110) to top surface 110, that is, along the height of capillary component 104. In this example, the observable signal may be a color change visible on top surface 110 of capillary component 104, indicating about 100% fluid advancement along the fluid path, that is, indicating that fluid has advanced about the entire height of capillary component 104.

Additionally or alternatively, the observable signal may comprise a change in color and/or color intensity of a signaling component comprised by the time-indicating device. For example, the signaling component may comprise one or more components configured to chemically react with and/or physically interact with (e.g., via physical dissolution) a component of the fluid to provide a change in color and/or color intensity. In this example, the signaling component may be provided at a position along the fluid path of the capillary component such that, when the fluid reaches the signaling component, a change in color and/or color intensity occurs, thus providing the observable signal. Additionally or alternatively, the observable signal may comprise a change in translucency, volume, and/or position of the signaling component.

For example, the signaling component may comprise a hydrogel having a first non-translucent (i.e., opaque) state. In this example, upon contact with a component of the fluid, the hydrogel may have a second state, such as a transparent state. In this example, the observable signal may be the change in translucency of the signaling component from the first state to the second state.

In another non-limiting example, the signaling component may comprise a hydrogel having a first state corresponding with a first volume. In this example, upon contact with a component of the fluid, the hydrogel may swell to a second state corresponding with a second volume that is larger than the first volume. In this example, the observable signal may be the change in volume of the signaling component from the first state to the second state.

In another non-limiting example, the signaling component may comprise a dissolvable component having an observable color. The signaling component may be provided at a position along the fluid path of the capillary component such that, when the fluid reaches the signaling component, the dissolvable component dissolves therein and thus travels with the fluid along the fluid path. In this example, the observable signal may be a change in position of the signaling component relative to the fluid path.

In one non-limiting example, capillary component 104 may comprise a sheet of base material with a coating of sorbent thereon as described herein. In this example, the sorbent coating is in fluid communication with application member 102 at least at a first end 107 as described herein. The sorbent may further comprise a signaling component at a second end 108 such that, when the fluid reaches the signaling component after advancement along the length 106 of capillary component 104, a change in color and/or color intensity occurs, thus providing the observable signal.

In another non-limiting example, capillary component 104 may comprise a sorbent without a base material as described herein. In this example, top surface 110 of capillary component 104 may comprise a signaling component such that, when fluid reaches the signaling component after advancement from application member 102, a change in color and/or color intensity occurs on top surface 110 of capillary component 104, thus providing the observable signal.

Example materials useful for the signaling component include, but are not limited to, materials having a first state and a second state upon contact with the fluid (such as an antiseptic solution), wherein the first state is different from the second state. For example, the first state may be a first color or color intensity, and the second state may be a second color or color intensity that is different from the first color or color intensity, as described herein. Additionally or alternatively, the first state may be a first translucency (i.e., translucent, transparent, or non-translucent, also referred to herein as opaque) and the second state may be a second translucency that is different from the first translucency, as described herein. Additionally or alternatively, the first state may be a first volume and the second state may be a second volume that is different from the first volume, as described herein. Additionally or alternatively, the first state may be a first position and the second state may be a second position that is different from the first position, as described herein.

Examples of signaling components useful according to the present disclosure include, but are not limited to, tinting agents as described herein. In one non-limiting example, the signaling component may comprise a tinting agent. In this example, the tinting agent may have a first color that is not easily observable at a low quantity and a second color that is easily observable, wherein the second color occurs when the tinting agent is dissolved with an aqueous or alcoholic solution, as described herein. It should be understood that in this example, the observable signal comprises the presence of the second color.

The sorbent may be directly affixed to, adhered to, and/or integrated with the application member and/or body (such as a flange component thereof) as described herein. In some non-limiting examples, the sorbent may be glued, melted, welded, molded, attached with an attachment mechanism, or sprayed to the application member and/or body, or a combination thereof. Example attachment mechanisms include, but are not limited to, pins, tacks, and combinations thereof. Additionally or alternatively, the sorbent may be provided as a coating on a base material as described herein, wherein the base material is affixed to, adhered to, and/or integrated with the application member and/or body (such as a flange component thereof) as described herein. According to some aspects, the sorbent and/or base material may have a shape that conforms to the shape of the application member, such as a shape having at least one dimension that is equal to or less than a corresponding dimension of the application member and/or a shape that is approximately the same shape as the shape of the application member. The capillary component may be provided in a position relative to the application member such that the sorbent does not contact the surface to which a fluid (e.g., an antiseptic solution) is applied by the application member when the applicator is in use.

It should be understood that in the example shown in FIG. 1, the time-indicating device is an "open system." As used herein, the term "open system" refers to a system, such as a time-indicating device, wherein fluid advancing along a fluid path is open to a surrounding environment.

According to some aspects, the time-indicating device may be provided as a closed system. As used herein, the term "closed system" refers to a system, such as a time-indicating device, wherein fluid advancing along a fluid path is separated from a surrounding environment.

Figure 2A:
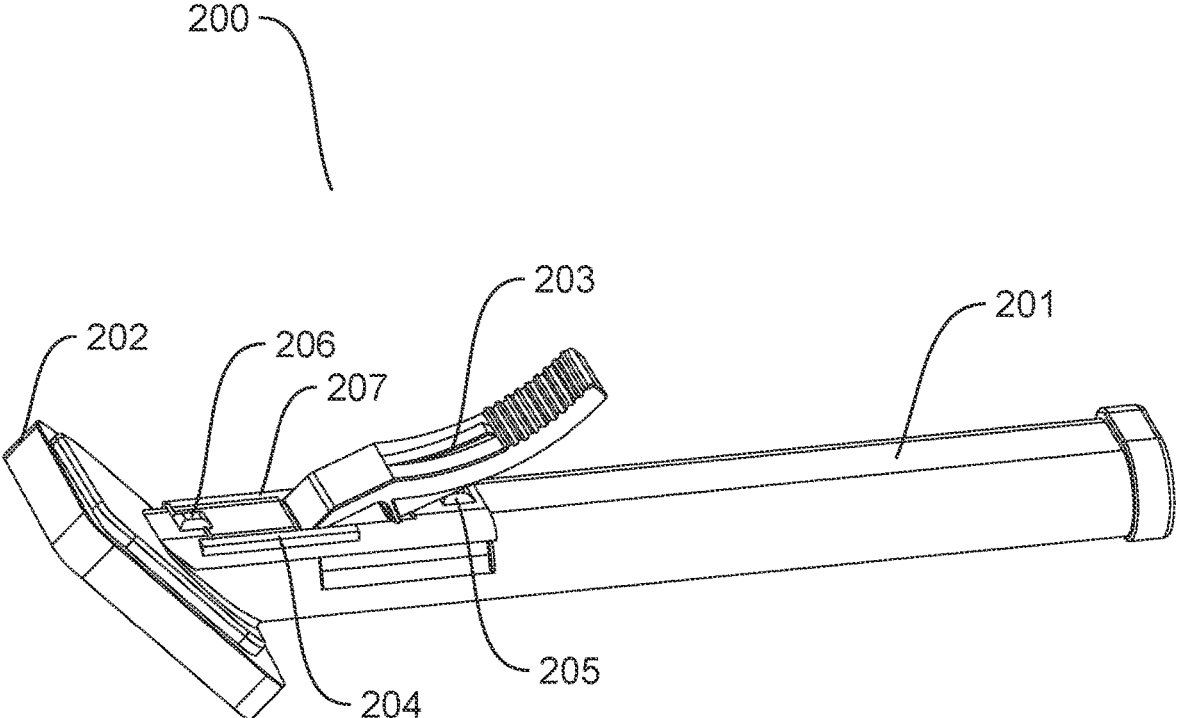
FIG. 2A shows an example applicator comprising a time-indicating device, according to aspects of the present disclosure.

For example, FIG. 2A shows an example of a closed system as described herein. Similar to the example shown in FIG. 1, FIG. 2A shows an example applicator 200 having a body 201, an application member 202, and an actuator 203 as described herein. In this example, the time-indicating device may comprise a capillary conduit 204 forming a fluid path as described herein. Specifically, capillary conduit 204 is a conduit having a length to diameter ratio sufficient to achieve capillary action. It should be understood that in this example, fluid advancing along the fluid path (i.e., flowing through the conduit) is separated from an external environment by at least the material of the capillary conduit, thus creating a closed system.

Example materials useful for the capillary conduit include, but are not limited to, glass, plastic, paper (including paper with and without a lining and/or coating), foil (such as a metal foil), plasticized and/or non-plasticized polymeric materials (such as acrylics), and combinations thereof.

The example time-indicating device shown in FIG. 2A may further comprise a fluid signaling component provided in an actuatable container. As used herein, the term "actuatable container" refers to a container configured to contain a substance (e.g., a fluid signaling component) and configured to release the substance upon actuation. According to some aspects, the actuatable container may be orientation-sensitive such that it controllably releases its contents when provided in a certain orientation (for example, in a vertical orientation). Additionally or alternatively, the actuatable container may be a frangible, pressure-sensitive container configured to controllably release its contents when a certain level of pressure is applied thereto.

For example, FIG. 2A shows an example of an actuatable container 205 provided in a position relative to actuator 203 such that, upon actuation of actuator 203 (i.e., upon depression of the lever in this example), actuator 203 provides a force on actuatable container 205 sufficient to fracture actuatable container 205. In this way, the substance contained in actuatable container 205 (e.g., the fluid signaling component) is released.

Example actuatable containers useful according to the present disclosure include, but are not limited to, ampoules (such as glass ampoules) and blister packs.

Example materials useful for the actuatable container include, but are not limited to, glass; polymers such as polyvinyl chloride (PVC), polyvinylidene chloride (PVDC), polychlorotrifluoroethylene (PCTFE), cyclic olefin copolymers (COC) or polymers (COP), polypropylene (PP), polyethylene (PE), polyamide (e.g., nylon), methacrylate modified acrylonitrile butadiene styrene (ABS), and glycol-modified polyethylene terephthalate (PET); metals such as aluminum; foils thereof; laminates thereof; and combinations thereof.

According to some aspects, the actuatable container may be configured such that actuation of the applicator concomitantly delivers fluid (e.g., an antiseptic solution) from the body to the application member as described herein and releases a fluid signaling component from the actuatable container. For example, as shown in FIG. 2A, actuatable container 205 is provided in a position relative to actuator 203 such that actuation of the applicator delivers fluid (such as an antiseptic solution) from body 201 to application member 202 as described herein while simultaneously or about simultaneously releasing the fluid signaling component from actuatable container 205 as described herein.

Example materials useful for the fluid signaling component include, but are not limited to, water, glycerin, glycol, alcoholic solutions, aqueous solutions, and combinations thereof. According to some aspects, the fluid signaling component may be tinted, for example, via a tinting agent as described herein. Alternatively, the fluid signaling component may be non-tinted.

According to some aspects, the actuatable container may be in direct or indirect selective fluid communication with the capillary component as described herein.

Figure 2B:
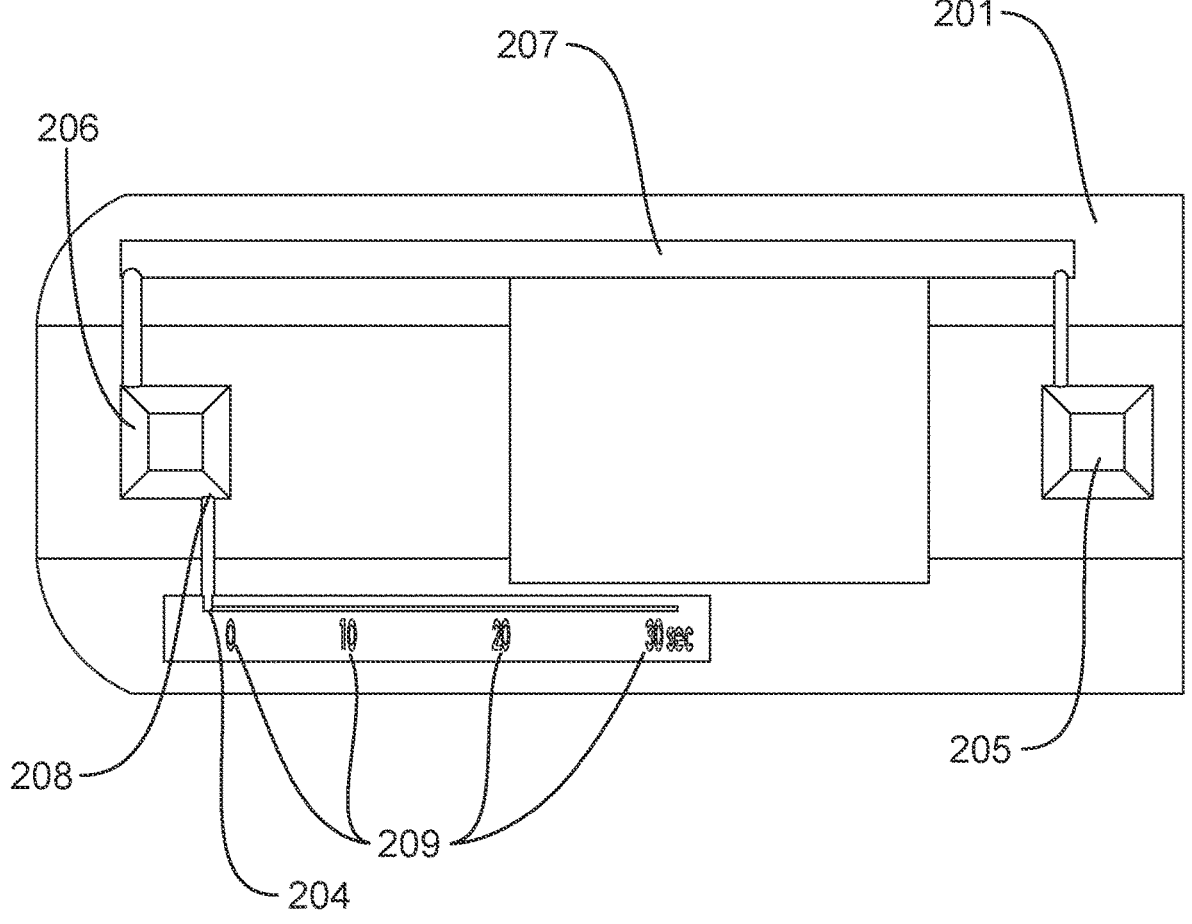
FIG. 2B shows a top view of an example applicator comprising a time-indicating device, according to aspects of the present disclosure.

For example, FIG. 2A shows an example wherein actuatable container 205 is in indirect fluid communication with capillary conduit 204 via a fluid reservoir 206 and fluid channel 207. This may be visualized, for example, in FIG. 2B, which shows a top-view perspective of the time-indicating device of FIG. 2A. As shown in FIG. 2B, upon actuation of an actuator, a fluid signaling component may be released from actuatable container 205 into and along fluid channel 207 until it reaches fluid reservoir 206. Fluid reservoir 206 may be in fluid communication with capillary conduit 204 via a restrictive aperture 208. Restrictive aperture 208 may have a size and/or orientation such that fluid contained in fluid reservoir 206 may pass through restrictive aperture 208 upon motion of the applicator. Fluid passing through restrictive aperture 208 may enter capillary conduit 204 and advance along the fluid path (i.e., through the conduit) via capillary action, as described herein.

It should be understood that fluid advancement along the fluid path of capillary conduit 204 may indirectly or directly provide an observable signal as described herein. For example, the observable signal may comprise the fluid signaling component advancing to a selected point along the length of capillary conduit 204, such as about the entire length of the fluid path (e.g., about the entire length of capillary conduit 204), as described herein. As shown in FIGS. 2A and 2B, capillary conduit 204 may be configured such that fluid advancing therethrough may be visible to a user.

It should also be understood that while FIGS. 2A and 2B show components of the time-indicating device (e.g., actuatable container 205, capillary conduit 204, reservoir 206, and fluid channel 207) provided proximal an external surface of body 201, one or more of the components may be provided inside body 201. In the example wherein at least capillary conduit 204 is provided inside body 201, the observable signal may indicate the fluid signaling component advancing to a selected point along the length of capillary conduit 204 at an application indicator location, such as a window, level sensor, or other gauge observable to a user.

According to some aspects, the time-indicating device may comprise one or more reference markings 209 as shown in FIG. 2B. Reference markings 209 may cue a certain fluid advancement along the fluid path and may correspond with one or more application periods as will be described herein. In this example, the observable signal may correspond with fluid advancing to a location marked by a reference marking, thus indicating an end of a certain application period. It should be understood that while the example shown in FIG. 2B shows reference markings 209 corresponding to 0, 10, 20, and 30 seconds, the time-indicating device may comprise additional or alternative markings sufficient to indicate an appropriate application period.

Figure 2C:
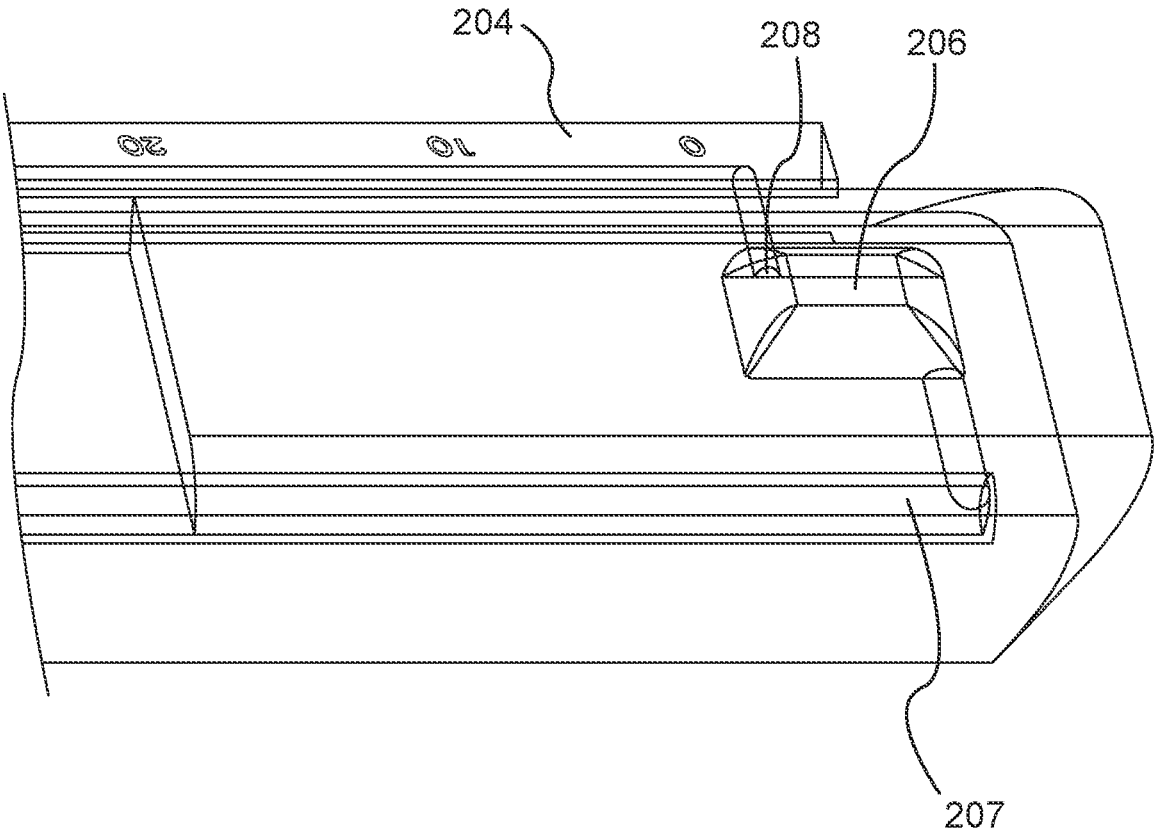
FIG. 2C shows a three-dimensional view of an example applicator comprising a time-indicating device, according to aspects of the present disclosure.

FIG. 2C shows a three-dimensional view of the examples shown in FIGS. 2A and 2B. In particular, FIG. 2C shows fluid channel 207 and fluid reservoir 206, as described herein. As shown in FIG. 2C, fluid reservoir 206 is in fluid communication with capillary conduit 204 via a restrictive aperture 208, as described herein.

Figure 2D:
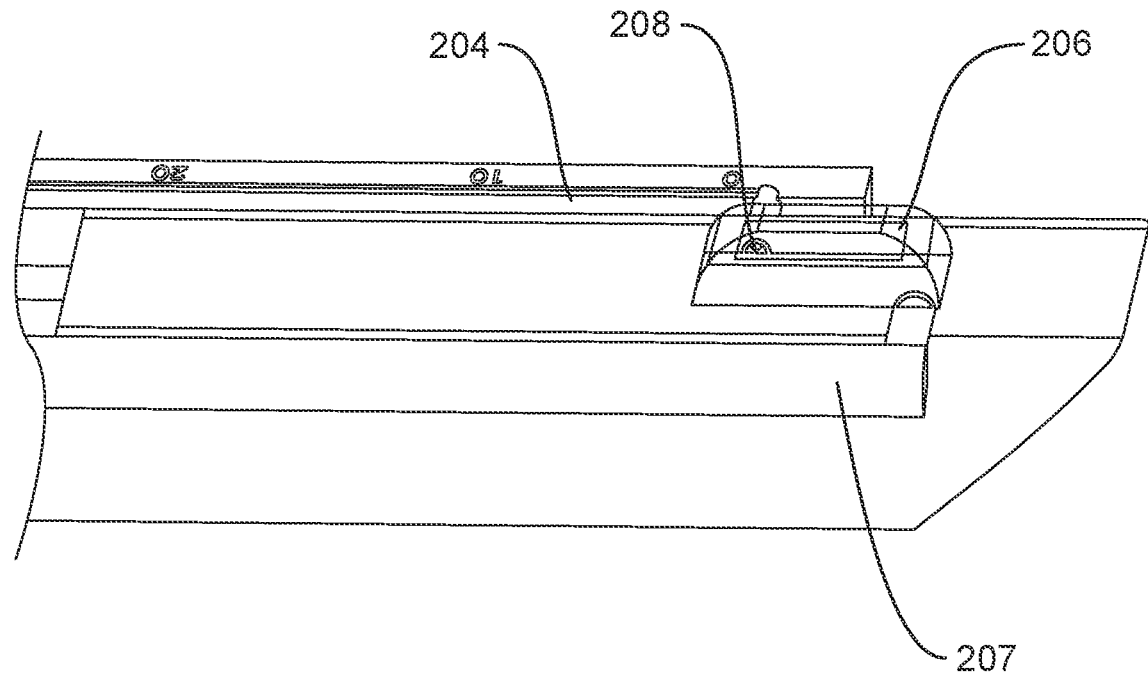
FIG. 2D shows a three-dimensional view of an example applicator comprising a time-indicating device, according to aspects of the present disclosure.

FIG. 2D shows another three-dimensional view of the examples shown in FIGS. 2A-2C. In particular, FIG. 2D shows fluid channel 207, fluid reservoir 206, restrictive aperture 208, and capillary conduit 204 as described herein.

Figure 2E:
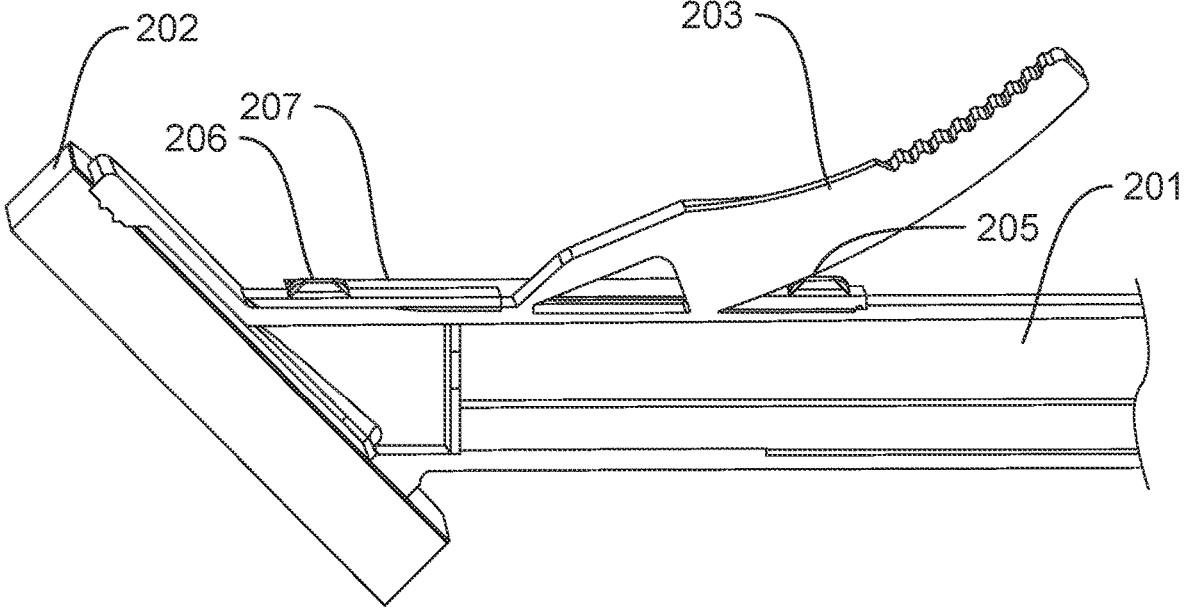
FIG. 2E shows a side view of an example applicator comprising a time-indicating device, according to aspects of the present disclosure.

FIG. 2E shows a side view of the examples shown in FIGS. 2A-2D, including body 201, application member 202, actuator 203, actuatable container 205, fluid channel 207, and fluid reservoir 206, as described herein.

Additionally or alternatively, the observable signal may comprise a change in color, color intensity, translucency, volume, and/or position of a second signaling component.

For In one non-limiting example, the second signaling component may comprise one or more components configured to chemically react with and/or physically interact with (e.g., via physical dissolution) the first fluid signaling component to provide a change in color and/or color intensity. In this example, the second signaling component may comprise a tinting agent, such as a powder having a first, colorless state. The second signaling component may be provided at a position along the fluid path of the capillary component such that, when the first fluid signaling component reaches the second signaling component, the second signaling component dissolves therein sufficient to provide a change in color and/or color intensity to the first fluid signaling component, thus providing the observable signal as described herein.

In another non-limiting example, the second signaling component may comprise a textile having a first state, such as a first color. In this example, the first fluid signaling component may provide a wetting mark to the textile upon contact, the wetting mark having a different color from the first color. In this example, the observable signal may be the appearance of the wetting mark.

In another non-limiting example, the second signaling component may comprise a hydrogel having a first non-translucent (i.e., opaque) state. In this example, upon contact with the first fluid signaling component, the hydrogel may have a second state, such as a transparent state. In this example, the observable signal may be the change in translucency of the second signaling component from the first state to the second state.

In another non-limiting example, the second signaling component may comprise a hydrogel having a first state corresponding to a first volume. In this example, upon contact with the first fluid signaling component, the hydrogel may swell to a second state corresponding to a second volume that is larger than the first volume. In this example, the observable signal may be the change in volume of the second signaling component from the first state to the second state.

In another non-limiting example, the second signaling component may comprise a dissolvable component having an observable color. The second signaling component may be provided at a position along the fluid path of the capillary component such that, when the first fluid signaling component reaches the second signaling component, the dissolvable component dissolves therein and thus travels with the first fluid signaling component along the fluid path. In this example, the observable signal may be a change in position of the second signaling component relative to the fluid path.

Example materials useful for the second signaling component include, but are not limited to, materials having a first state and a second state upon contact with the first fluid signaling component, wherein the first state is different from the second state. For example, the first state may be a first color, and the second state may be a second color that is different from the first color, as described herein. Additionally or alternatively, the first state may be a first translucency (i.e., translucent, transparent, or non-translucent, also referred to herein as opaque) and the second state may be a second translucency that is different from the first translucency, as described herein. Additionally or alternatively, the first state may be a first volume and the second state may be a second volume that is different from the first volume, as described herein. Additionally or alternatively, the first state may be a first position and the second state may be a second position that is different from the first position, as described herein.

The time-indicating device of the present disclosure may be configured to provide at least a first observable signal upon a certain physical and/or chemical event as described herein, wherein the physical and/or chemical event signifies a certain application period. As used herein, the term "application period" refers to a time period during which a fluid contained by the applicator (e.g., an antiseptic solution) is applied to a surface via the application member. It should be understood that application of the fluid to a surface will require delivering the fluid from the body to the application member, which may be accomplished via actuating an actuator as described herein and/or by providing the applicator is a certain orientation, for example, in a vertical position.

According to some aspects, time-indicating device of the present disclosure may be configured to provide second, third, or more observable signals in order to signify the end of second, third, or more certain application periods, respectively. The second, third, or more observable signals may be the same and/or different from at least one other observable signal providable by the time-indicating device. In one non-limiting example, the first observable signal may correspond with a first degree of fluid advancement along the fluid path as described herein. In this example, the second observable signal may correspond with a second degree of fluid advancement along the fluid path as described herein, the second degree being greater than the first degree. In this way, the time indicating-device may be configured to signify two, three, or more different applications periods as described herein.

According to some aspects, the certain application period may be the period of time required for an antiseptic solution as described herein to provide an acceptable antimicrobial effect. In one non-limiting example, the application period may correspond with a time required for an antiseptic solution as described herein to provide an acceptable log reduction in microbial load when applied to a surface, such as the surface of a medical device or the surface of an animal or human body.

In some non-limiting examples, the certain application period may be about 30 seconds, optionally about 45 seconds, optionally about 60 seconds, optionally about 75 seconds, optionally about 90 seconds, optionally about 105 seconds, optionally about 120 seconds, optionally about 135 seconds, optionally about 150 seconds, optionally about 165 seconds, optionally about 180 seconds, optionally about 195 seconds, and optionally about 210 seconds. According to some aspects, the certain application period may be between about 30 seconds and 3 minutes.

Additionally or alternatively, the certain application period may the time required for the antiseptic solution to provide a 1-log reduction in microbial load, optionally about a 2-log reduction in microbial load, optionally about a 3-log reduction in microbial load, and optionally about a 4-log reduction in microbial load.

It should be understood that the certain application period may depend at least in part on the identity of the antiseptic solution, such as its efficacy against microbes as described herein.

According to some aspects, the time-indicating device may be configured such that the rate of fluid advancement along the capillary component's fluid path may be sufficient to reliably measure a certain application period. The rate of fluid advancement along the capillary component's fluid path may depend at least in part on one or more physical and/or chemical properties of the capillary component and/or of the fluid. Example physical and/or chemical properties include, but are not limited to, porosity of a sorbent, polarity of a fluid (e.g., polarity of the solvent comprised by the antiseptic solution and/or polarity of the fluid signaling component), polarity of a sorbent, one or more dimensions of the fluid path, shape of the fluid path, chemical composition of the fluid path, and combinations thereof.

In one non-limiting example, the rate of fluid advancement along the capillary component's fluid path may be selected by selecting a combination of a sorbent having a certain polarity (including a non-polar sorbent) and a fluid having a certain polarity. In this example, the rate of fluid advancement may be highest when the polarity of the sorbent most nearly matches the polarity of the fluid, whereas the rate of fluid advancement may be the lowest when the polarity of the sorbent is most different from the polarity of the fluid.

Additionally or alternatively, the rate of fluid advancement along the capillary component's fluid path may be selected by selecting a certain dimension of the fluid path, such as the width and/or length of the fluid path. Additionally or alternatively, the rate of fluid advancement along the capillary component's fluid path may be selected by selecting a certain shape of the fluid path, such as a straight fluid path and/or a tortuous fluid path.

Additionally or alternatively, the rate of fluid advancement along the capillary component's fluid path may be selected by selecting a certain chemical composition of the fluid path. For example, a fluid-contacting surface of the fluid path may be provided with one or more chemical additives having properties that may aid or hinder fluid advancement along the fluid path. In one non-limiting example, the chemical additive may affect the polarity of a fluid-contacting surface of the fluid path, which may affect the rate of fluid advancement along the fluid path as described herein.

According to some aspects, the time-indicating device may be provided as an integrated component of the applicator, for example, as shown in FIGS. 1 and 2A-2E. In some non-limiting examples, the time-indicating device may be molded as part of the applicator. Additionally or alternatively, at least a portion of the time-indicating device may be provided as a disparate device configured to adjoin with an applicator via a connector. For example, the time-indicating device may comprise a base material and/or sorbent as described herein which is disparate from an applicator. The base material and/or sorbent layer may be configured such that it may be affixed and/or adhered to an applicator via a connector prior to use. Example connectors include, but are not limited to, adhesives, snaps, fasteners (e.g., male and female fasteners), wraps (such as hook and loop wraps), straps, applicator housings, and combinations thereof.

According to some aspects, the time-indicating device may be provided within the visual field of a user when the user is operating the applicator as intended. For example, as shown in FIG. 1, the base material and/or sorbent may be provided proximal to a surface of the application member that is observable to a user when the user is applying a fluid to a surface. In another example, as shown in FIGS. 2A-2E, the capillary conduit may be provided at a location of the body that is observable to a user when the user is applying a fluid to a surface.

According to some aspects, the time-indicating device may be free of any components incompatible with an antiseptic solution as described herein. For example, the time-indicating device may be free of any electrical components and/or energy sources that may provide an ignition source for a flammable solution. According to some aspects, the time-indicating device may be free of any combustible material.

The present disclosure is also directed to applicators comprising a time-indicating device as described herein.

The present disclosure is also directed to method of using the time-indicating device and/or applicator as described herein. According to some aspects, the method comprises providing an applicator having a time-indicating device as described as described herein, actuating the applicator in order to apply a fluid to a surface, and observing the time-indicating device for an observable signal. The method may further comprising discontinuing application of the fluid when the observable signal has been observed or after the observable signal has been observed.

While the aspects described herein have been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects, as set forth above, are intended to be illustrative, not limiting. Various changes may be made without departing from the spirit and scope of the disclosure. Therefore, the disclosure is intended to embrace all known or later-developed alternatives, modifications, variations, improvements, and/or substantial equivalents.

Thus, the claims are not intended to be limited to the aspects shown herein, but are to be accorded the full scope consistent with the language of the claims, wherein reference to an element in the singular is not intended to mean "one and only one" unless specifically so stated, but rather "one or more." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

Further, the word "example" is used herein to mean "serving as an example, instance, or illustration." Any aspect described herein as "example" is not necessarily to be construed as preferred or advantageous over other aspects. Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C. Nothing disclosed herein is intended to be dedicated to the public regardless of whether such disclosure is explicitly recited in the claims.

The word "about" is used herein to mean within ±5% of the stated value, optionally within ±4%, optionally within ±3%, optionally within ±2%, optionally within ±1%, optionally within ±0.5%, optionally within ±0.1%, and optionally within ±0.01%.

What is claimed is:

1. An applicator comprising:
a body configured to house a fluid;
an application member in selective fluid communication with the body; and
a time-indicating device, wherein:
the time-indicating device comprises a capillary conduit having a fluid path,

the time-indicating device is configured such that fluid advancement along the fluid path provides at least a first observable signal signifying a first certain application period, and the time-indicating device further comprises a fluid signaling component provided in an actuatable container, wherein the actuatable container is in direct or indirect selective fluid communication with the capillary conduit such that upon actuation of the actuatable container, the fluid signaling component is transferred to the capillary conduit.

2. An applicator comprising:
a body configured to house a fluid;
an application member in selective fluid communication with the body; and
a time-indicating device, wherein:
the time-indicating device comprises a capillary component having a fluid path,
the capillary component comprises a sorbent in fluid communication with the application member,
the time-indicating device is configured such that fluid advancement along the fluid path provides at least a first observable signal,
the first observable signal signifies a first certain application period and comprises a color and/or color intensity change of the sorbent, and
the applicator is configured such that fluid advancement along the fluid path is visible to a user.

3. The applicator according to claim 2, wherein the sorbent comprises a signaling component provided at a position along the fluid path, and
wherein the first observable signal comprises a change in color, color intensity, translucency, volume, or position of the signaling component.

4. The applicator according to claim 1,
wherein the applicator further comprises an actuator configured to actuate the applicator such that the body is provided in fluid communication with the application member, and
wherein the actuatable container is provided in a position relative to the actuator such that actuation of the applicator corresponds with actuation of the actuatable container.

5. The applicator according to claim 1, wherein the actuatable container is orientation-sensitive such that the actuatable container controllably releases the fluid signaling component therefrom when the applicator is provided in a first orientation.

6. The applicator according to claim 1, wherein the time-indicating device further comprises:
a fluid channel in selective fluid communication with the actuatable container, and
a fluid reservoir in fluid communication with the fluid channel and in fluid communication with the capillary conduit via a restrictive aperture.

7. The applicator according to claim 1, wherein the fluid is an antiseptic solution comprising at least one antiseptic agent and a solvent.

8. The applicator according to claim 7, wherein the first certain application period is a period of time required for the antiseptic solution to provide an acceptable antimicrobial effect, wherein the period of time is between about 30 seconds and 3 minutes.

9. A method of applying a fluid to a surface, the method comprising:
providing an applicator comprising:
a body configured to house a fluid,

an application member in selective fluid communication with the body, and
a time-indicating device, wherein:
the time-indicating device comprises a capillary conduit having a fluid path,
the time-indicating device is configured such that fluid advancement along the fluid path provides at least a first observable signal signifying a first certain application period, and
the time-indicating device further comprises a fluid signaling component provided in an actuatable container, wherein the actuatable container is in direct or indirect selective fluid communication with the capillary conduit such that upon actuation of the actuatable container, the fluid signaling component is transferred to the capillary conduit;
actuating the applicator in order to apply the fluid to a surface; and
observing the time-indicating device for the first observable signal.

10. A method of applying a fluid to a surface, the method comprising:
providing an applicator comprising:
a body configured to house a fluid,
an application member in selective fluid communication with the body, and
a time-indicating device, wherein:
the time-indicating device comprises a capillary component having a fluid path,
the capillary component comprises a sorbent in fluid communication with the application member,
the time-indicating device is configured such that fluid advancement along the fluid path provides at least a first observable signal,
the first observable signal signifies a first certain application period and comprises a color and/or color intensity change of the sorbent, and
fluid advancement along the fluid path is visible to a user;
actuating the applicator in order to apply the fluid to a surface; and
observing the time-indicating device for the first observable signal.

11. The method according to claim 10, wherein the sorbent comprises a signaling component provided at a position along the fluid path, and
wherein the first observable signal comprises a change in color and/or color intensity of the signaling component.

12. The method according to claim 9,
wherein the applicator further comprises an actuator configured to actuate the applicator such that the body is provided in fluid communication with the application member, and
wherein the actuatable container is provided in a position relative to the actuator such that actuation of the applicator corresponds with actuation of the actuatable container.

13. The method according to claim 9, wherein the actuatable container is orientation-sensitive such that the actuatable container controllably releases the fluid signaling component therefrom when the applicator is provided in a first orientation.

14. The method according to claim 9, wherein the time-indicating device further comprises:
a fluid channel in selective fluid communication with the actuatable container, and a fluid reservoir in fluid communication with the fluid channel and in fluid communication with the capillary conduit via a restrictive aperture.

15. The method according to claim 9, wherein the fluid is an antiseptic solution comprising at least one antiseptic agent and a solvent.

16. The method according to claim 15, wherein the first certain application period is a period of time required for the antiseptic solution to provide an acceptable antimicrobial effect, wherein the period of time is between about 30 seconds and 3 minutes.

\* \* \* \* \*